United States Patent
Miculka et al.

(10) Patent No.: US 6,696,555 B1
(45) Date of Patent: Feb. 24, 2004

(54) 3'-DESOXYPENTOPYRANOSYL NUCLEIC ACID, ITS PRODUCTION AND ITS USE

(75) Inventors: Christian Miculka, Vienna (AT); Thomas Wagner, Constance (DE); Norbert Windhab, Hattersheim/Main (DE)

(73) Assignee: Nanogen Recognomics GmbH, Frankfurt (DE)

( * ) Notice: Subject to any disclaimer, the term of this patent is extended or adjusted under 35 U.S.C. 154(b) by 0 days.

(21) Appl. No.: 09/762,977

(22) PCT Filed: Aug. 18, 1999

(86) PCT No.: PCT/EP99/06036

§ 371 (c)(1),
(2), (4) Date: Apr. 19, 2001

(87) PCT Pub. No.: WO00/11011

PCT Pub. Date: Mar. 2, 2000

(30) Foreign Application Priority Data

Aug. 18, 1998 (DE) .......................... 198 37 387

(51) Int. Cl.[7] .................. C07H 21/00; C07H 19/06; C07H 19/16
(52) U.S. Cl. .................. 536/23.1; 536/24.3; 536/24.5; 536/25.34; 536/27.1; 536/27.11; 536/28.1; 435/91.1
(58) Field of Search ............... 530/23.1, 24.3, 530/24.5, 25.34, 27.1, 28.1, 27.11; 435/91.1

(56) References Cited

U.S. PATENT DOCUMENTS 4,476,301 A * 10/1984 Imbach et al. .......... 536/27.21

(List continued on next page.)

FOREIGN PATENT DOCUMENTS

DE 19619373 A1 11/1997

(List continued on next page.)

OTHER PUBLICATIONS

Khripach et al., "Glycosylation of $N^4$Benzoylcytosine and $N^6$-Benzoyladenine by Acetals Glycals," *Khim. Geterotsikl. Soedin(Russian)*, (Issue No. 1), pp. 111–117 (1982). Month of publication data is unavailable from the document copy supplied. Issue No. information is provided whenever possible following the vol. No in parentheses.*

(List continued on next page.)

*Primary Examiner*—James O. Wilson
*Assistant Examiner*—Lawrence E Crane
(74) *Attorney, Agent, or Firm*—O'Melveny & Myers LLP

(57) ABSTRACT

The invention relates to a 3'-deoxypentopyranosylnucleic acid consisting essentially of 3'-deoxypentopyranosylnucleosides of the formulae (I) or of the formulae (II)

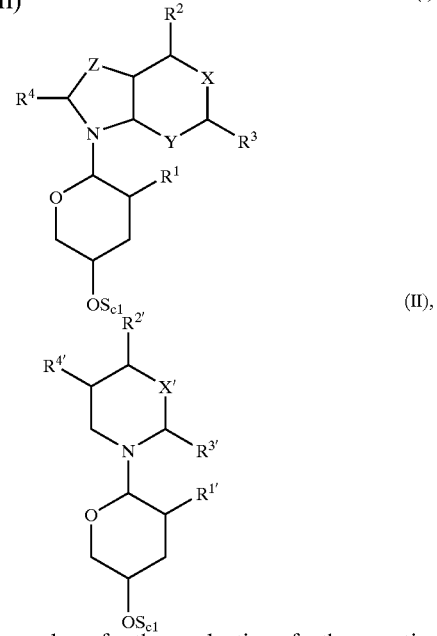

their preparation and use for the production of a therapeutic, diagnostic and/or electronic component.

15 Claims, 4 Drawing Sheets

U.S. PATENT DOCUMENTS

| | | | | |
|---|---|---|---|---|
| 5,250,529 | A | * 10/1993 | Theoharides | 514/254.07 |
| 5,821,259 | A | * 10/1998 | Theoharides | 514/396 |
| 6,248,753 | B1 | * 6/2001 | Chen | 514/303 |
| 6,255,310 | B1 | * 7/2001 | Webb et al. | 514/258 |
| 6,271,380 | B1 | * 8/2001 | Gilligan et al. | 546/118 |
| 6,288,060 | B1 | * 9/2001 | Webb et al. | 514/235.8 |
| 6,319,900 | B1 | * 11/2001 | Wei et al. | 514/12 |
| 6,323,312 | B1 | * 11/2001 | Rivier | 530/306 |
| 2001/0007867 | A1 | * 7/2001 | Chen | 514/180 |

FOREIGN PATENT DOCUMENTS

| | | |
|---|---|---|
| DE | 19651560 A1 | 6/1998 |
| DE | 198 37 387.2 | * 8/1998 |
| WO | WO 98/25943 | 6/1996 |
| WO | WO 96/40711 | 12/1996 |
| WO | W O 00/11011 A1 | * 3/2000 |

OTHER PUBLICATIONS

Watanabe et al., "Nucleosides. 118. Total Synthesis of Pentopyranine B and D. Cytosine Nucleosides Elaborated by *Streptomyces griseochromogenes,*" *Canadian Journal of Chemistry*, 59, 468–472 (1981). Month of publication data is unavailable from the document copy supplied. Issue No. information is provided whenever possible following the vol. No. in parentheses.*

Seto et al., "The Structure of Pentopyranines A and C. Two Cytosine Nucleosides with α–L–Configuration," *Agricultural & Biological Chemistry*, 37(10), 2421–2426 (1973). Month of publication data is unavailable from the document copy supplied. Issue No. information is provided whenever possible following the vol. No. in parentheses.*

Böhringer et al., "110. Warum Pentose– unde Nicht Hexose–Nucleinsäure? Oligonucleotide aus 2',3'–Dideoxy–β–D–glucopyuranosyl–Bausteinen ('Homo–DNA) Herstellung," *Helvetica Chimica Acta*(German), 75(5), 1416–1477 (1992). Month of publication data is unavailable from the document copy supplied. Issue No. information is provided whenever possible following the vol. No. in parentheses.*

Schlönvogt et al., "Pyranosyl RNA ('p–RNA'): NMR and Molecular–Dynamics Study of the Duplex Formed by Self––pairing of Ribopyranosyl–(C–G–A–A–T–T–C–G)," *Helvetica Chimica Acta*, 79(8), 2316–2342 (1996). Month of publication data is unavailable from the document copy supplied. Issue No. information is provided whenever possible following the vol. No. in parentheses.*

Jenny et al., "N$^2$Isobutyryl–O$^6$–[2–(p–nitrophenyl)ethyl] guanine: A New Building Block for the Efficient Synthesis of Carbocyclic Guanosine Analogs," *Nucleosides & Nucleotides*, 11(6), 1257–1261 (1992). Month of publication data is unavailable from the document copy supplied. Issue No. information is provided whenever possible following the vol. No. in parentheses.*

Brown et al., "Modern Machine–aided Methods of Oligodeoxyribonucleotide Synthesis," Chapter 1 in *Oligonucleotides and Analogues—A Practical Approach*, P. Eckstein (ed.), IRL Press, New York, NY, 1991; only pp. 1–24 supplied. Month of publication data is unavailable from the document copy supplied. Issue No. information is provided whenever possible following the vol. No. in parentheses.*

Gait et al., "Oligoribonucleotide Synthesis," Chapter 2 in *Oligonucleotides and Analogues—A Practical Approach*, P. Eckstein (ed.), IRL Press, New York, NY, 1991; only pp. 25–48 supplied. Month of publication data is unavailable from the document copy supplied. Issue No. information is provided whenever possible following the vol. No. in parentheses.*

Aerschot, Arthur, et al., "1,5–Anhydrohexit–Nucleinsäsuren, neue potentielle Antisense–Wirkstoffe." Angew. Chem. 107(12): 1483–85 (1995).

Aerschot, Arthur, et al., "1,5–Anhydrohexitol Nucleic Acids, a New Promising Antisense Construct," Angew Chem. Int. Ed. Engl. 34(12):1338–1339, 2165 (1995).

Anon, "126111t How does homo–DNA help us to understand the structure of DNA?" Chemical Abstracts 122 (1995), Abstract No. 126111t, p. 403.

De Winter, H., et al. "Molecular Dynamics Simulation to Investigate Differences in Minor Groove Hydration of HNA/RNA Hybrids as Compared to HNA/DNA Complexes." J. Am. Chem. Soc. 120: 5381–94 (1998); ACS web publ. date: May 19, 1998.

Diederichsen, Ulf. "Ladungstransport in DNA: eine Kontroverse." Angew. Chem. 109(21):2411–2413 (1997).

Diederichsen, Ulf, "Charge Transfer in DNA: A Controversy," Angew Chem. Int. Ed. Engl. 36(21):2317–2319 (1997).

Eschenmoser, Albert. "126110s Toward a chemical etiology of the natural nucleic acid structure" Chemical Abstracts 122: 403 (1995); p. 403, Abstr. No. 126110s.

Eschenomoser, Albert, et al. "19. Warum Pentose—und nicht Hexose–Nucleinsäuren? Einleitung und Problemstellung, Konformationsanalyse für Oligonucleotid–Ketten aus 2',3'–Dideoxyglucopyranosyl–Bausteinen ('Homo–DNS') sowie Betrachtungen zur Konformation von A– und B–DNS." Helvetica Chemica Acta 75:218–59 (1992).

Goodnow, Robert A., et al. "Synthesis of Thymine, Cytosine, Adenine, and Guanine Containing N–Fmoc Protected Amino Acids: Building Blocks for Construction of Novel Oligonucleotide Backbone Analogs." Tetrahedron Letters 38(18):3195–98 (1997).

Goodnow, Robert A., et al. "Oligomer Synthesis and DNA/RNA Recognition Properties of a Novel Oligonucleotide Backbone Analog: Glycopyranosyl Nucleic Amide (GNA)." Tetrahedron Letters 38(18): 3199–3202 (1997).

Hendrix, Chris, et al. ",5'–Anhydrohexitol Oligonucleotides: Hybridisation and Strand Displacement with Oligoribonucleotides, Interaction with Rnase H and HIV Reverse Transcriptase." Chem. Eur. J. 3(9): 1513–20 (1997).

Hunziker, Jürg, et al. "18, Warum Pentose—und nicht Hexose–Nucleinsäuren? Oligo(2', 3'–dideoxy–β–D–glucopyranosyl) nucleotide ('Homo–DNS'): Paarungseigenschaften." Helvetica Chemica Acta 76: 259–352 (Feb. 10, 1993).

Okahata, Yoshio, et al. "Anisotropic Electric Conductivity in an Aligned DNA Cast Film." J. Am. Chem. Soc. 120: 6165–66 (1998).

Otting, Gottfried, et al. "Warum Pentose—und nicht Hexose–Nucleinsäuren. 'Homo–DNS': $^1$H–, $^{13}$C–, $^{31}$P– und $^{15}$N–NMR–spektroskopische Untersuchung von ddGlc(A–A–A–A–A–T–T–T–T–T) in wässriger Lösung." Helvetica Chemica Acta 76: 2701–56 (1993) (Dec. 15, 1993).

B. Doboszewski et al, "Easy Synthesis and Different Conformational Behavior of Purine and Pyrimidine β–D–glycero–Pent–2'–enopyranosyl Nucleosides", J. Org. Chem., 1995, vol. 60, No. 24, also referred to as XP 002122435.

Diekmann et al, "Didesoxy–ribonucleoside durch Schmelzkondensation", J. Prakt. Chem., vol. 335, No. 5, 1993, pp. 415–424, also referred to as XP000569335.

K.A. Watanabe et al, "Total Syntheses of Pentopyranine A, an $_\alpha$–L Cytosine Nucleoside Elaborated by *Streptomyces griseochromogenes*", J. Org. Chem. vol. 39, No. 17, 1974, pp. 2482–2486, also referred to as XP002122438.

A. Bolli et al, "Pyranosyl–RNA:Further Observations on Replication", Helvetica Chimica Acta, vol. 80, 1997, No. 6, pp. 1901–1951, also referred to as XP002096832.

B. Doboszewski et al, "Synthesis of 3'–Deoxy–3—Hydroxymethyl–aldopentopyranosyl Nucleosides and their Incorporation in Oligonucleotides", Tetrahedron vol. 51, No. 45, pp. 12319–12336, also referred to as XP002096831; (1995).

S. Pitch et al, "Pyranosyl–RNA (p–RNA): Base Pairing Selectivity and Potential to Replicate", Helvetica Chimica Acta, vol. 78, No. 7, pp. 1621–1635, also referred to as XP002096830; (1995).

Eschenmoser et al, "Why Pentose and Not Hexose Nucleic Acids", vol. 76, pp. 2161–2183, also referred to as XP002094190. (1993) Helv. Chim. Acta.

\* cited by examiner

3'-DESOXYPENTOPYRANOSYL NUCLEIC ACID, ITS PRODUCTION AND ITS USE

This application is a national stage application filed under 35 U.S.C. §371 of PCT International Application No. PCT/EP99/06036, filed on Aug. 18, 1999 and which claims priority from German Application No. 198 37 387.2, filed Aug. 18, 1998.

The present invention relates to a 3'-deoxypentopyranosylnucleic acid consisting essentially of 3'-deoxypentopyranosylnucleosides of the formula (I) or of the formula (II)

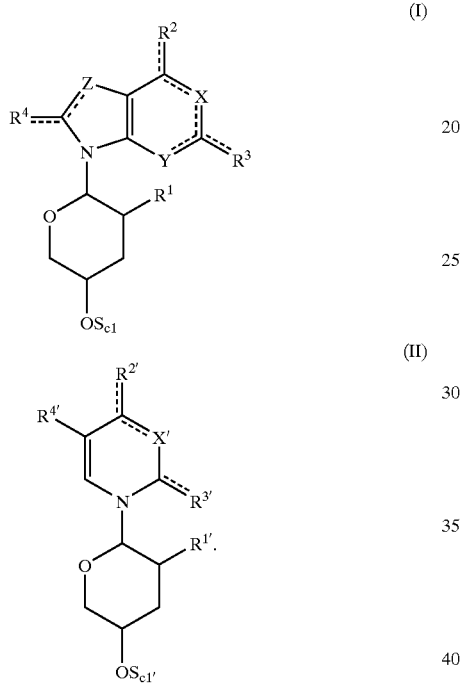

their preparation and use for the production of a therapeutic, diagnostic and/or electronic component.

Pyranosylnucleic acids (p-NAs) are structural types which in general are isomeric to the natural RNA and in which the pentose units are present in the pyranose form and are repetitively linked between positions C-2' and C-4' by phosphodiester groups. "Nucleobase" is understood here as meaning the canonical nucleobases A, T, U, C, G, but also the pairs isoguanine/isocytosine and 2,6-diaminopurine/xanthine and, within the meaning of the present invention, also other purines and pyrimidines. p-NAs, to be precise the p-RNAs derived from ribose, were described for the first time by Eschenmoser et al. (Helv. Chim. Acta 1993, 76, 2161; Helv. Chim Acta 1995, 78, 1621; Angew. Chem. 1996, 108, 1619–1623). They exclusively form so-called Watson-Crick-paired, i.e. purine-pyrimidine- and purine-purine-paired, antiparallel, reversibly "melting", quasi-linear and stable duplices. Homochiral p-RNA strands of opposite chiral sense likewise pair controllably and are strictly non-helical in the duplex formed. This specificity, which is valuable for the synthesis of supramolecular units, is associated with the relatively low flexibility of the ribopyranose phosphate backbone and with the high inclination of the base plane to the strand axis and the tendency resulting from this for intercatenary base stacking in the resulting duplex and can finally be attributed to the participation of a 2',4'-cis-disubstituted ribopyranose ring in the synthesis of the backbone. These essentially better pairing properties make p-NAs preferred pairing systems compared with DNA and RNA for application in the synthesis of supramolecular units. They form a pairing system which is orthogonal to natural nucleic acids, i.e. they do not pair with the DNAs and RNAs occurring in the natural form, which is particularly of importance in the diagnostic field.

p-RNA, however, has the following disadvantages which are to be attributed to the presence of the 3'-hydroxyl function:

1. The necessary protection of the 3'-hydroxyl group with a benzoyl protective group complicates and prolongs the synthetic route to the monomeric units considerably.
2. On account of the use of the allyl radical as a base and phosphate protective group, the deprotection and the removal of the oligonucleotide must be carried out by two successively connected steps. First, the allyl radicals are removed by the Noyori method (R. Noyori, J. Am. Chem. Soc. 1990, 112, 1691–6). Then the base-labile acyl groups must be cleaved and the oligonucleotide removed from the carrier.
3. After oligonucleotide synthesis is complete, the cleavage of the 3'-benzoyl radicals from the oligonucleotide causes difficulties. In order to remove these radicals effectively the use of hydrazine is necessary, which can lead to ring-opening of the pyrimidine bases, especially uracil and thymine.
4. In the synthesis of the oligonucleotides, 5-(4-nitrophenyl)-1H-tetrazole is employed as a coupling reagent in the automated p-RNA synthesis. The concentration of this reagent in the solution of tetrazole in acetonitrile is so high here that in general the 5-(4-nitrophenyl)-1H-tetrazole crystallizes out in the thin tubing of the synthesizer and the synthesis thus comes to a premature end. Moreover, it was observed that the oligomers were contaminated with 5-(4-nitrophenyl)-1H-tetrazole. The benzimidazolium triflate alternatively used also has negative points: it crystallizes out, even though rarely, in the tubing, is expensive and must moreover be recrystallized before its use.

The object of the present invention was therefore to provide and to oligomerize novel pentopyranosylnucleosides for orthogonal pairing systems, whereby the disadvantages described above can be circumvented.

Surprisingly, it has now been found that 3'-deoxypentopyranosylnucleic acids (p-DNA) do not have the disadvantages described and still have the advantageous orthogonal pairing properties (see FIG. 3).

A subject of the present invention is therefore a 3'-deoxypentopyranosylnucleic acid consisting essentially of 3'-deoxypentopyranosylnucleosides of the formula (I),

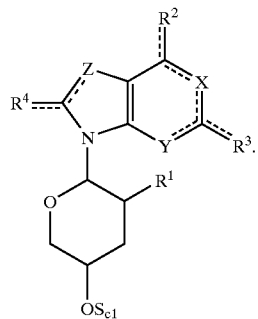

(I)

in which
R¹ is equal to H, OH, Hal where Hal is equal to Br or Cl, a radical selected from

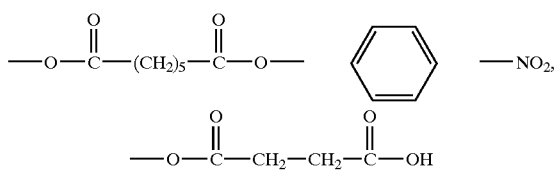

or —O—P[N(i-Pr)$_2$] (OCH$_2$CH$_2$CN) where i-Pr is equal to isopropyl, or —O—PH—(=O)(—O), R², R³ and R⁴ independently of one another, identically or differently, are in each case H, NR⁵R⁶, OR⁷, SR⁸, =O, C$_n$H$_{2n+1}$ where n is an integer from 1–12, preferably 1–8, in particular 1–4, a β-eliminable group, preferably a group of the formula —OCH$_2$CH$_2$R¹⁸ where R¹⁸ is equal to a cyano or p-nitrophenyl radical or a fluorenylmethyloxycarbonyl (Fmoc) radical, or (C$_n$H$_{2n}$)NR¹⁰R¹¹ where R¹⁰R¹¹ is equal to H, C$_n$H$_{2n+1}$ or R¹⁰R¹¹ is bonded via a radical of the formula

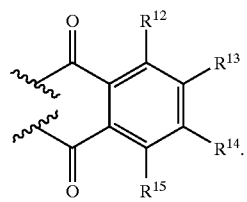

(III)

in which R¹², R¹³, R¹⁴ and R¹⁵ independently of one another, identically or differently, are in each case H, OR⁷, where R⁷ has the abovementioned meaning, or C$_n$H$_{2+1}$, or C$_n$H$_{2-1}$, where n has the abovementioned meaning, and R⁵, R⁶, R⁷ and R⁸ independently of one another, identically or differently, are in each case H, C$_n$H$_{2n+1}$, or C$_n$H$_{2n-1}$, where n has the above-mentioned meaning, —C(O)R⁹ where R⁹ is equal to a linear or branched, optionally substituted alkyl or aryl radical, preferably a phenyl radical, X, Y, and Z independently of one another, identically or differently, are in each case =N-, =C(R¹⁶)- or —N(R¹⁷)- where R¹⁶ and R¹⁷ independently of one another, identically or differently, are in each case H or C$_n$H$_{2n+1}$ or (C$_n$H$_{2n}$)NR¹⁰R¹¹ with the abovementioned meanings, the dotted lines represent optional unsaturation, and S$_{c1}$ is hydrogen or a protective group selected from an acyl, trityl, allyloxycarbonyl, a photolabile or β-eliminable protective group, preferably a fluorenymethyloxycarbonyl (Fmoc) or 4, 4'-dimethoxytrityl (DMT) group, or of the formula (II)

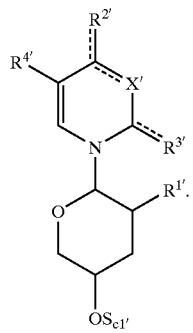

(II)

in which R¹' is equal to H, OH, Hal where Hal is equal to Br or Cl, a radical selected from

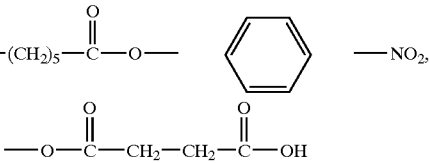

or —O—P[N(i-Pr)$_2$] (OCH$_2$CH$_2$CN) where i-Pr is equal to isopropyl, or —O—PH—(=O)(—O)

R²', R³', and R⁴' independently of one another, identically or differently, are in each case H, =O, C$_n$H$_{2n+1}$ or OC$_n$H$_{2n-1}$, a β-eliminable group, preferably a group of the formula —OCH$_2$CH$_2$R¹⁸ where R¹⁸ is equal to a cyano or p-nitrophenyl radical or a fluorenylmethyloxycarbonyl (Fmoc) radical or (C$_n$H$_{2n}$)NR¹⁰'R¹¹', where R¹⁰', R¹¹', independently of one another has the abovementioned meaning of R¹⁰ or R¹¹, and X', Y', and Z' independently of one another, identically or differently, are in each case =N—, =C(R¹⁶')— or —N(R¹⁷'), where R¹⁶'and R¹⁷'independently of one another have the abovementioned meaning of R¹⁶ and R¹⁷, the dotted lines represent optional unsaturation, and S$_{c1'}$, has the abovementioned meaning of S$_{c1}$.

According to the present invention, the nucleic acid according to the invention is synthesized from 3'-deoxypentopyranosylnucleosides, further modifications, such as the conjugates described in greater detail below, likewise being included by the invention.

The 3'-deoxypentopyranosylnucleosides are in general 3'-deoxyribo-, 3'-deoxyarabino-, 3'-deoxylyxo- and/or 3'-deoxyxylopyranosylnucleosides, preferably 3'-deoxyribopyranosyl-nucleosides, where the 3'-deoxypentopyranosyl part can be of D configuration, but also of L configuration.

Customarily, the 3'-deoxypentopyranosylnucleosides are 3'-deoxypentopyranosylpurine, -2,6-diaminopurine, -6-purinethiol, -pyridine, -pyrimidine, -adenosine, -guanosine, -isoguanosine, -6-thioguanosine, -xanthine, -hypoxanthine, -thymidine, -cytosine, -isocytosine, -indole, -tryptamine, -N-phthaloyltryptamine, -uracil, -caffeine, -theobromine, -theophylline, -benzotriazole or -acridine, in particular 3'-deoxypentopyranosylpurine, -pyrimidine, -adenosine, -guanosine, -thymidine, -cytosine, tryptamine, -N-phthalotryptamine or -uracil.

The compounds include 3'-deoxypentopyranosylnucleosides which can be used as linkers, i.e. as compounds having functional groups which can bind covalently to biomolecules, such as, nucleic acids occurring in their natural form or modified nucleic acids, such as DNA, RNA but also p-NAs, preferably p-DNAs.

For example, among these are included 3'-deoxypentopyranosylnucleosides in which $R^2$, $R^3$, $R^4$, $R^{2'}$, $R^{3'}$ and/or $R^{4'}$ is a 2-phthalimidoethyl or allyloxy radical. Preferred linkers according to the present invention are, for example, uracil-based linkers in which the 5-position of the uracil has preferably been modified, e.g. N-phthaloylaminoethyluracil, but also indole-based linkers, preferably tryptamine derivatives, such as N-phthaloyltryptamine.

Moreover, the present invention includes 3'-deoxypentopyranosylnucleosides which carry a protective group, preferably an acid-, base-, photolabile- or β-eliminable protective group, in particular a trityl group, particularly preferably a dimethoxytrityl group, exclusively on the 4'-oxygen atom of the 3'-deoxypentopyranoside moiety.

The following compounds are preferred examples of pentopyranosylnucleosides which can be present in the nucleic acid according to the invention, or are particularly suitable for its preparation:

A) [(2',4'-Di-O-benzoyl)-3'-deoxy-β-ribopyranosyl] nucleosides, in particular a [(2',4'-di-O-benzoyl)-3'-deoxy-β-ribopyranosyl]adenine, -guanine, -cytosine, -thymidine, -uracil, -xanthine or -hypoxanthine, and also an N-benzoyl-2',4'-di-O-benzoyl-3'-deoxyribopyranosylnucleoside, in particular an -adenine, -guanine or -cytosine, and also an N-isobutyroyl-2',4'-di-O-benzyl-3'-deoxyribopyranosylnucleoside, in particular an -adenine, -guanine or -cytosine, and also an $O^6$-(2-cyanoethyl)-$N^2$-isobutyroyl-2',4'-di-O-benzoyl-3'-deoxyribopyranosylnucleoside, in particular a -guanine, and also an $O^6$-(2-(4-nitrophenyl)ethyl)-$N^2$-isobutyroyl-2',4'-di-O-benzoyl-3'-deoxyribopyranosylnucleoside, in particular a -guanine.

B) 3'-Deoxy-β-ribopyranosylnucleosides, in particular a 3'-deoxy-β-ribopyranosyladenine, -guanine, -cytosine, -thymidine, -uracil, -xanthine or hypoxanthine, and an N-benzoyl-, N-isobutyroyl-, $O^6$-(2-cyanoethyl)- or $O^6$-(2-(4-nitrophenyl)ethyl)-$N^2$-isobutyroyl-3'-deoxy-β-ribopyranosylnucleoside, in particular a -guanine.

C) 4'-DMT-3'-deoxypentopyranosylnucleosides, preferably a 4'-DMT-3'-deoxy-ribopyranosylnucleoside, in particular a 4'-DMT-3'-deoxyribopyranosyladenine, -guanine, -cytosine, -thymidine, -uracil, -xanthine or -hypoxanthine, and also an N-benzoyl-4'-DMT-3'-deoxyribopyranosylnucleoside, in particular N-benzoyl-4'-DMT-3'-deoxyribopyranosyl-adenine, -guanine or -cytosine, and also an N-isobutyroyl-4'-DMT-3'-deoxyribopyranosylnucleoside, in particular an N-isobutyroyl-4'-DMT-3'-deoxyribopyranosyladenine, -guanine or -cytosine and also an $O^6$-(2-cyanoethyl)-$N^2$-isobutyroyl-4'-DMT-3'-deoxyribopyranosylnucleoside, in particular an $O^6$-(2-cyanoethyl)-$N^2$-isobutyroyl-4'-DMT-3'-deoxyribopyranosylguanine, and also an $O^6$-(2-(4-nitrophenyl)ethyl)-$N^2$-isobutyroyl-4'-DMT-3'-deoxyribopyranosylnucleoside, in particular an $O^6$-(2-(4-nitrophenyl)ethyl)-$N^2$-isobutyroyl-4'-DMT-3'-deoxyribopyranosylguanine.

D) 3'-Deoxy-β-ribopyranosyl-N,N'-dibenzoyladenosine or 3'-deoxy-β-ribopyranosyl-N,N'-dibenzoylguanosine.

Suitable precursors for the oligonucleotide synthesis are, for example, 4'-DMT-3'-deoxypentopyranosylnucleosides-2'-phosphitamide/-H-phosphonate, preferably a 4'-DMT-3'-deoxyribopyranosylnucleoside-2'-phosphitamide/-H-phosphonate, in particular 4'-DMT-3'-deoxyribopyranosyladenine-, -guanine-, -cytosine-, -thymidine-, -xanthine-, -hypoxanthine-, or -uracil-2'-phosphitamide/-H-phosphonate, and also an N-benzoyl-4'-DMT-3'-deoxyribopyranosyladenine-, -guanine- or -cytosine-2'-phosphitamide/-H-phosphonate and also an N-isobutyroyl-4'-DMT-3'-deoxyribopyranosyladenine-, -guanine- or -cytosine-2'-phosphitamide/-H-phosphonate, $O^6$-(2-cyanoethyl)-4'-DMT-3'-deoxyribopyranosylguanine-, -xanthine-, -hypoxanthine-2'-phosphitamide/-H-phosphonate or $O^6$-(2-(4-nitrophenyl)ethyl)-$N^2$-isobutyroyl-4'-DMT-3'-deoxyribopyranosylguanine, and for the coupling to the solid carrier, for example, 4'-DMT-3'-deoxypentopyranosylnucleosides-2'-succinate, preferably a 4'-DMT-3'-deoxyribopyranosylnucleoside-2'-succinate, in particular 4'-DMT-3'-deoxyribopyranosyladenine-, -guanine-, -cytosine-, -thymidine-, -xanthine-, -hypoxanthine- or -uracil-2'-succinate and also an N-benzoyl-4'-DMT-3'-deoxyribopyranosyladenine-, -guanine- or -cytosine-2'-succinate and also an N-isobutyroyl-4'-DMT-3'-deoxyribopyranosyladenine-, -guanine- or -cytosine-2'-succinate, O-(2-cyanoethyl)-4'-DMT-3'-deoxyribopyranosylguanine-2'-succinate and also an $O^6$-(2-(4-nitrophenyl)ethyl)-$N^2$-isobutyroyl-4'-DMT-3'-deoxyribopyranosylguanine-2'-succinate.

The 3'-deoxyribopyranosylnucleosides can be prepared, for example, by a process in which (a) an optionally protected nucleobase is reacted with a protected 3'-deoxyribopyranose, (b) the protective groups are cleaved from the 3'-deoxyribopyranosyl moiety of the product from step (a) and, if appropriate, (c) the product from step (b) is protected in the 4'-position of the 3'-deoxypentopyranoside.

In a particular embodiment, the 3'-deoxypyranosylnucleoside is protected by a protective group $S_{c1}$, or $S_{c1'}$ which is acid-labile, base-labile, photolabile, β-eliminable or cleavable by metal catalysis.

In general, the protective groups mentioned are a β-eliminable protective group, preferably a fluorenylmethyloxycarbonyl (Fmoc) group, a photolabile group, an acyl group, preferably an acetyl, benzoyl, nitrobenzoyl and/or methoxybenzoyl group, or trityl groups, preferably a 4,4'-dimethoxytrityl (DMT) group.

The introduction of a DMT group is thus carried out, for example, by reaction with DMTCl in the presence of a base, e.g. of N-ethyldiisopropylamine (Hünig base), and, for example, of pyridine, methylene chloride or a pyridine/methylene chloride mixture at room temperature.

In general, the preferably anomerically pure ribopyranosyl structural unit is prepared starting from 1,2-O-isopropylidene-5-O-triphenylmethyl-α-D-xyloftiranose (1 in FIG. 1) according to known processes (W. Sowa, Can. J. Chem, 1968, 46, 1568; Z. J. Witczak et. al. Carbohydrate Research, 1982, 110. 326) but in general with improved yields. Analogously to the known process, 1 (FIG. 1) is tritylated and sodium hydride is preferably used instead of sodium hydroxide solution for the preparation of the methyl xanthate ester in the 3'-position (2 in FIG. 1). After removal of the methyl xanthate, the trityl and the isopropylidene protective groups are preferably cleaved using trifluoroacetic acid instead of the 80% glacial acetic acid described in the literature. The yields were in some cases improved considerably by means of these modifications.

In a further embodiment, a linker according to formula (II), in which $R^{4'}$ is $(C_nH_{2n})NR^{10'}R^{11'}$ and $R^{10'}R^{11'}$ is linked via a radical of the formula (III) having the meaning already designated, is advantageously prepared by the following process:

(a) a compound of the formula (II) where $R^{4'}$ is equal to $(C_nH_{2n})OS_{c3}$ or $(C_nH_{2n})Hal$, in which n has the above-mentioned meaning, $S_{c3}$ is a protective group, preferably a mesylate group, and Hal is chlorine or bromine, is reacted with an azide, preferably in DMF, then (b) the reaction product from (a), is preferably reduced with triphenylphosphine for example in pyridine, then (c) the reaction product from (b) is reacted with an appropriate phthalimide, e.g. N-ethoxycarbonylphthalimide, and (d) the reaction product from (c) is reacted with an appropriate protected pyranose, e.g. 2',4'-di-O-benzoyl-3'-deoxyribopyranose, and finally (e) the protective groups are cleaved, e.g. with methylate, and (f) the further steps are carried out as already described above.

In addition, indole derivatives as linkers have the advantage of the ability to fluoresce and are therefore particularly preferred for nanotechnology applications in which it may be a matter of detecting very small amounts of substance. Thus, indole-1-ribosides have already been described in N. N. Suvorov et al., Biol. Aktivn. Soedin., Akad. Nauk SSSR 1965, 60 and Tetrahedron 1967, 23, 4653. However, there is no analogous process for preparing 3-substituted derivatives. In general, their preparation takes place via the formation of an aminal of the unprotected sugar component and an indoline, which is then converted into the indole-1-riboside by oxidation. For example, indole-1-glucosides and -1-arabinosides have been described (Y. V. Dobriynin et al, Khim.-Farm. Zh. 1978, 12, 33), whose 3-substituted derivatives were usually prepared by means of Vielsmeier reaction. This route for the introduction of aminoethyl units into the 3-position of the indole is too complicated, however, for industrial application.

In a further preferred embodiment, a linker according to formula (I), in which X and Y independently of one another, identically or differently, are in each case $=C(R^{16})$ where $R^{16}$ is equal to H or $C_nH_{2n}$ and $Z=C(R^{16})$- where $R^{16}$ is equal to $(C_nH_{2n})NR^{10'}R^{11'}$ is therefore advantageously prepared by the following process:

(a) the appropriate indoline, e.g. N-phthaloyltryptamine, is reacted with a pyranose, e.g. D-3'-deoxyribose, to give the nucleoside diol, then (b) the hydroxyl groups of the pyranosyl moiety of the product from (a) are preferably protected with acyl groups, e.g. by means of acetic anhydride, then (c) the product from (b) is oxidized, e.g. by 2,3-dichloro-5,6-dicyanoparaquinone, and (d) the hydroxyl protective groups of the pyranosyl moiety of the product from (c) are cleaved, for example, by means of methylate and then (e) the further steps as already described above are carried out.

In a further embodiment, the 4'- or 2'-protected, 3'-deoxypentopyranosylnucleosides are phosphitylated in a further step or bonded to a solid phase.

Phosphitylation is carried out, for example, by means of cyanoethyl N-diisopropylchlorophosphoramidite in the presence of a base, e.g. N-ethyldiisopropylamine or by means of phosphorus trichloride and imidazole or tetrazole and subsequent hydrolysis with addition of base. In the first case, the product is a phosphoramidite and in the second case an H-phosphonate. The bonding of a protected pentopyranosylnucleoside according to the invention to a solid phase, e.g. long-chain alkylamino controlled pore glass (CPG, Sigma Chemie, Munich) can be carried out, for example, via a succinoyl linker.

The compounds obtained can be used for the preparation of the 3'-deoxypentopyranosylnucleic acids according to the invention.

A further subject of the present invention is therefore a process for the preparation of a 3'-deoxypentopyranosylnucleic acid, having the following steps:

(a) in a first step, a protected 3'-deoxypentopyranosylnucleoside, such as already described above, is bonded to a solid phase and (b) in a second step the 4'-protected 3'-deoxypentopyranosylnucleoside bonded to a solid phase according to step (a) is lengthened by a 2'-phosphitylated 4'-protected 3'-deoxypentopyranosylnucleoside and, when using phosphoramidites, is then oxidized, for example, by an aqueous iodine solution, and (c) step (b) is repeated with identical or different phosphitylated 3'-, 4'-protected 3'-deoxypentopyranosylnucleosides until the desired 3'-deoxypentopyranosylnucleic acid is present.

When using H-phosphonates, the oxidation to the corresponding phosphoric acid diesters is in general carried out at the end of the reaction chain, e.g. by an aqueous iodine solution.

A suitable coupling reagent when using phosphoramidites is particularly pyridinium hydrochloride, as in contrast to coupling reagents customarily used no recrystallization of the coupling reagent, no blockage of the coupling reagent lines and a significantly more rapid condensation takes place.

Suitable coupling reagents when using H-phosphonates are particularly arylsulphonyl chlorides, diphenyl chlorophosphate, pivaloyl chloride or adamantoyl chloride.

A significant advantage of the H-phosphonate method is that no phosphate protective groups are needed. The acyl protective groups of the bases can be cleaved, for example, by aqueous ammonia. When using the 2-(4-nitrophenyl) ethyl radical as a protective group for the $O^6$-position of guanine, this can be removed, for example, without problems by treatment for about 40 minutes with 1M DBU.

It is furthermore advantageous that no protective group-cleaving hydrazinolysis of oligonucleotides is necessary, and thus no ring-opening is to be feared, especially in the case of uracil and thymine. The cyanoethyl radicals can be cleaved by aqueous ammonia together with the acyl protective groups of the bases. When using the 2-(4-nitrophenyl) ethyl radical as a protective group for the $O^6$-position of guanine, the radical can be removed without problems by treatment for about 40 minutes with 1M DBU.

In a further particular embodiment, pentofuranosylnucleosides e.g. the adenosine, guanosine, cytidine, thymidine and/or uracil occurring in its natural form, can also be incorporated in step (a) and/or step (b), which leads, for example, to a mixed p-DNA/DNA or p-DNA/RNA.

p-NAs and in particular the p-DNAs form stable duplices with one another and in general do not pair with the DNAs and RNAs occurring in their natural form. This property makes p-NAs preferred pairing systems.

Such pairing systems are supramolecular systems of non-covalent interaction, which are distinguished by selectivity, stability and reversibility, and whose properties are preferably influenced thermodynamically, i.e. by temperature, pH and concentration. Such pairing systems can also be used, for example, on account of their selective properties as a "molecular adhesive" for the bringing together of different metal clusters to give cluster associates having potentially novel properties [see, for example, R. L. Letsinger, et al., Nature 1996, 382, 607–9; P. G. Schultz et al., Nature 1996, 382, 609–11]. Consequently, the p-NAs are also suitable for use in the field of nanotechnology, for example for the preparation of novel materials, diagnostics and therapeutics and also microelectronic, photonic or optoelectronic components and for example the controlled bringing together of molecular species to give supramolecular units, such as for the (combinatorial) synthesis of protein assemblies [see, for example, A. Lombardi, J. W. Bryson, W. F. DeGrado, Biomolekuils (Pept. Sci.) 1997, 40, 495–504], as p-NAs form pairing systems which are strongly and thermodynamically controllable. A further application therefore arises, especially in the diagnostic and drug discovery field, due to the possibility of providing functional, preferably biological units such as proteins or DNA/RNA sections with a p-NA code which does not interfere with the natural nucleic acids (see, for example, WO93/20242).

Another subject of the invention is therefore the use of a 3'-deoxypentopyranosylnucleic acid according to the invention for the production of a medicament, in particular of a therapeutic, diagnostic and/or electronic component.

A biomolecule, e.g. DNA or RNA, can be used for non-covalent linking with another biomolecule, e.g. DNA or RNA, if both biomolecules contain sections which, as a result of complementary sequences of nucleobases, can bind to one another by formation of hydrogen bridges. Biomolecules of this type are used, for example, in analytical systems for signal amplification, where a DNA molecule whose sequence is to be analysed is on the one hand to be immobilized on a solid support by means of such a non-covalent DNA linker, and on the other hand is to be bonded to a signal-amplifying branched DNA molecule (bDNA) (see FIG. 3 in S. Urdea, Bio/Technol. 1994, 12, 926 or U.S. Pat. No. 5,624,802). A significant disadvantage of the last-described systems is that to date they are subject with respect to sensitivity to the processes for nucleic acid diagnosis by polymerase chain reaction (PCR) (K. Mullis, Methods Enzymol. 1987, 155, 335). This is to be attributed, inter alia, to the fact that the non-covalent bonding of the solid support to the DNA molecule to be analysed as well as the non-covalent bonding of the DNA molecule to be analysed does not always take place specifically, as a result of which a mixing of the functions "sequence recognition" and "non-covalent bonding" occurs. The use of p-NA's as an orthogonal pairing system which does not intervene in the DNA or RNA pairing process solves this problem advantageously, as a result of which the sensitivity of the analytical processes described can be markedly increased.

A further subject of the present invention is therefore a conjugate comprising a 3'-deoxypentopyranosylnucleoside of the formula (I) or (II) according to the invention and a biomolecule.

Biomolecule is understood within the meaning of the present invention as meaning a naturally occurring substance or a substance derived from a naturally occurring substance.

Conjugates within the meaning of the present invention are covalently bonded hybrids of p-NA's and other biomolecules, preferably a peptide, protein or a nucleic acid, for example an antibody or a functional moiety thereof or a DNA and/or RNA occurring in its natural form. Functional moieties of antibodies are, for example, Fv fragments (Skerra & Plückthun (1988) Science 240, 1038), single-chain Fv fragments (scFv; Bird et al. (1988), Science 242, 423; Huston et al. (1988) Proc. Natl. Acad. Sci. U.S.A., 85, 5879) or Fab fragments (Better et al. (1988) Science 240, 1041).

In a preferred embodiment, there are in this case p-DNA/DNA or p-DNA/RNA conjugates.

Conjugates are preferably used when the functions "sequence recognition" and "non-covalent bonding" must be realized in a molecule, since the conjugates according to the invention contain two pairing systems which are orthogonal to one another.

Both sequential and convergent processes are suitable for the preparation of conjugates.

In a sequential process, for example, for example after automated synthesis of a p-RNA oligomer has taken place directly on the same synthesizer—after readjustment of the reagents and of the coupling protocol—a DNA oligonucleotide, for example, is additionally synthesized. This process can also be carried out in the reverse sequence.

In a convergent process, for example, p-RNA oligomers having aminoterminal linkers and, for example, DNA oligomers having, for example, thiol linkers are synthesized in separate operations. An iodoacetylation of the p-DNA oligomer and the coupling of the two units according to the protocols known from the literature (T. Zhu et al., Bioconjug. Chem. 1994, 5, 312) is then preferably carried out.

Convergent processes prove to be particularly preferred on account of their flexibility. The term conjugate within the meaning of the present invention is also understood as meaning so-called arrays. Arrays are arrangements of immobilized recognition species which, especially in analysis and diagnosis, play an important role in the simultaneous determination of analytes. Examples are peptide arrays (Fodor et al., Nature 1993, 364, 555) and nucleic acid arrays (Southern et al. Genomics 1992, 13, 1008; Heller, U.S. Pat. No. 5,632,957). A higher flexibility of these arrays can be achieved by binding the recognition species to coding oligonucleotides and the associated, complementary strands to certain positions on a solid carrier. By applying the coded recognition species to the "anti-coded" solid carrier and adjustment of hybridization conditions, the recognition species are non-covalently bonded to the desired positions. As a result, various types of recognition species, such as DNA sections, antibodies, can only be arranged simultaneously on a solid carrier by use of hybridization conditions (see FIG. 4). As a prerequisite for this, however, codons and anticodons are necessary which are extremely strong and selective—in order to keep the coding sections as short as possible—and do not interfere with natural nucleic acids. p-NAs, preferably p-DNA's, are particularly advantageously suitable for this.

The present invention therefore also relates to a process using in which recognition species, preferably natural DNA or RNA strands and proteins, in this case preferably antibodies or functional moieties of antibodies, are clearly encoded by p-NA sections, preferably p-DNA sections. These can then be hybridized with the associated codons on a solid carrier according to FIG. 4. Thus, always novel, diagnostically useful arrays can be synthesized on a solid support which is equipped with codons in the form of an array merely by adjustment of hybridization conditions using always novel combinations of recognition species in the desired positions. If the analyte, for example a biological sample such as serum or the like, is then applied, the species to be detected are then bonded to the array in a certain pattern which can then be recorded indirectly (e.g. by fluorescence labelling of the recognition species) or directly (e.g. by impedance measurement at the point of linkage to the codon). The hybridization is then ended by suitable condition (temperature, salts, solvents, electrophoretic processes) so that again only the carrier with the codons remains. This is then again loaded with other recognition species and is used, for example, for the same analyte for the determination of another pattern. The always new arrangement of recognition species in the array format and the use of p-NAs as pairing systems is particularly advantageous compared with other systems, see, for example WO 96/13522 (see 16, below).

A further subject of the present invention therefore in particular also relates to a diagnostic and/or an electronic component comprising a conjugate according to the invention, as already described in greater detail above.

The following figures and examples are intended to describe the invention in greater detail without restricting it.

EXAMPLES

Example 1

Figure 1:
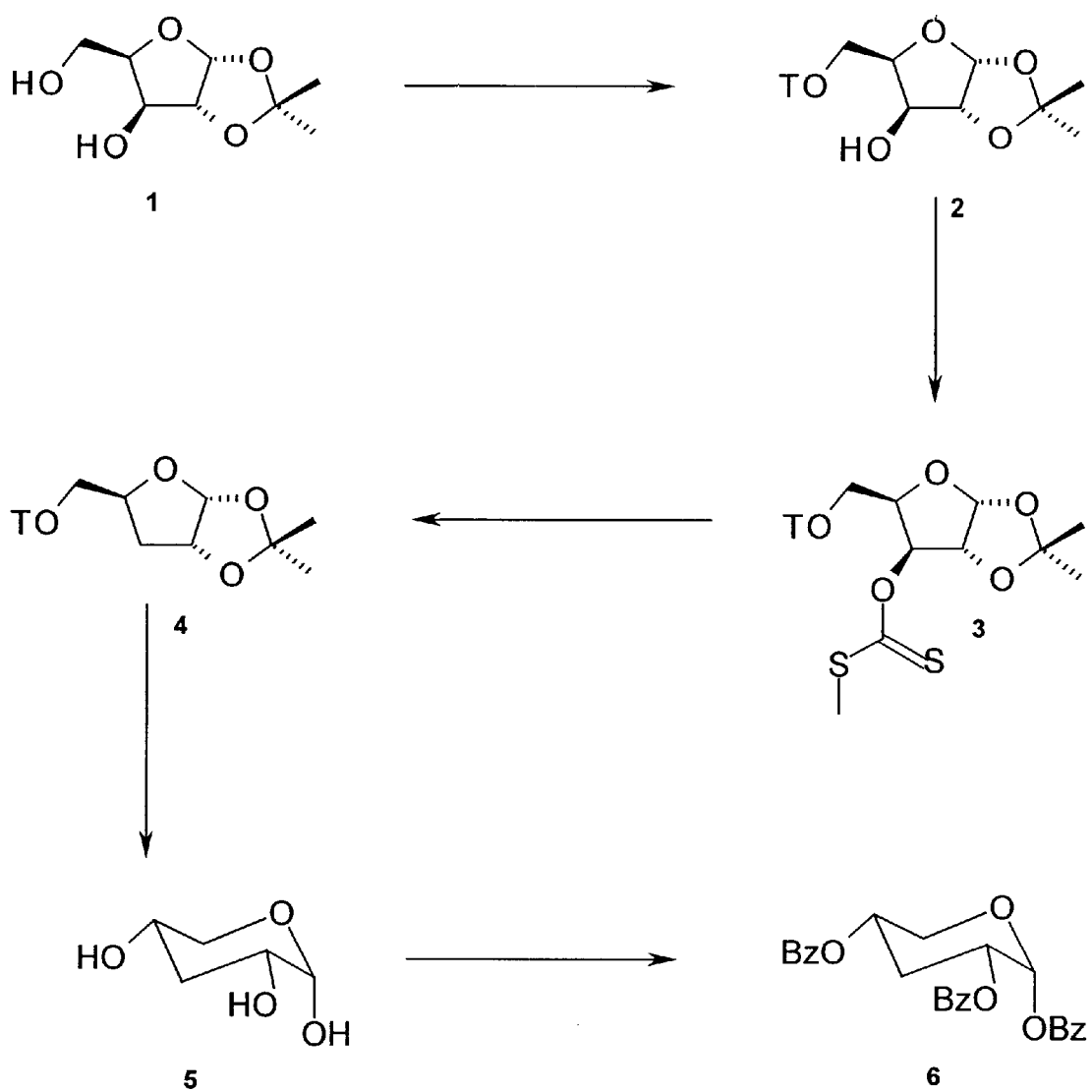
FIG. 1 shows the synthesis of the sugar components, T being triphenylmethyl (trityl).
Figure 2:
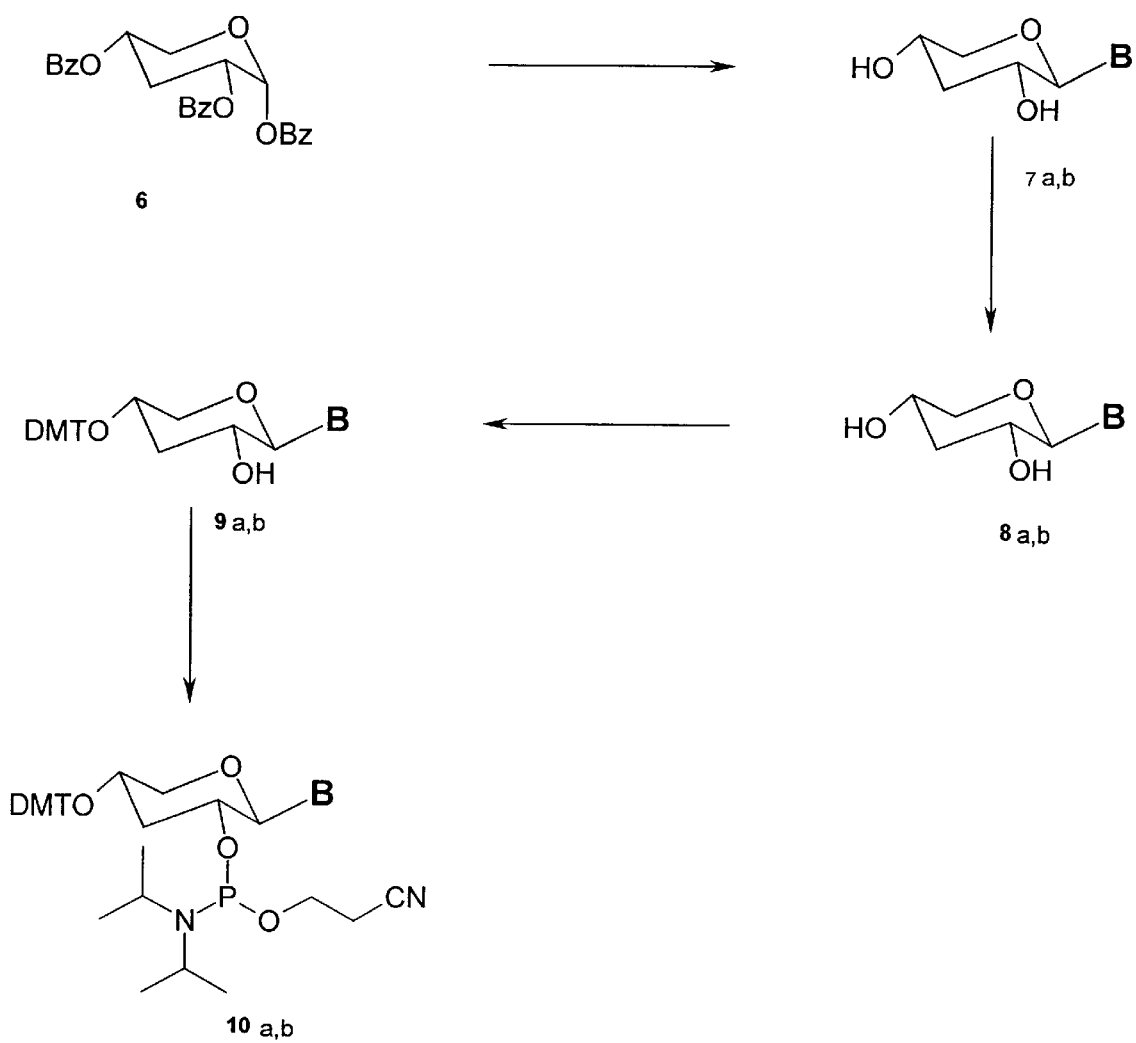
FIG. 2 shows the synthesis route to the monomeric structural units, B being a nucleobase occurring in nature or a synthetic nucleobase.
Figure 3:
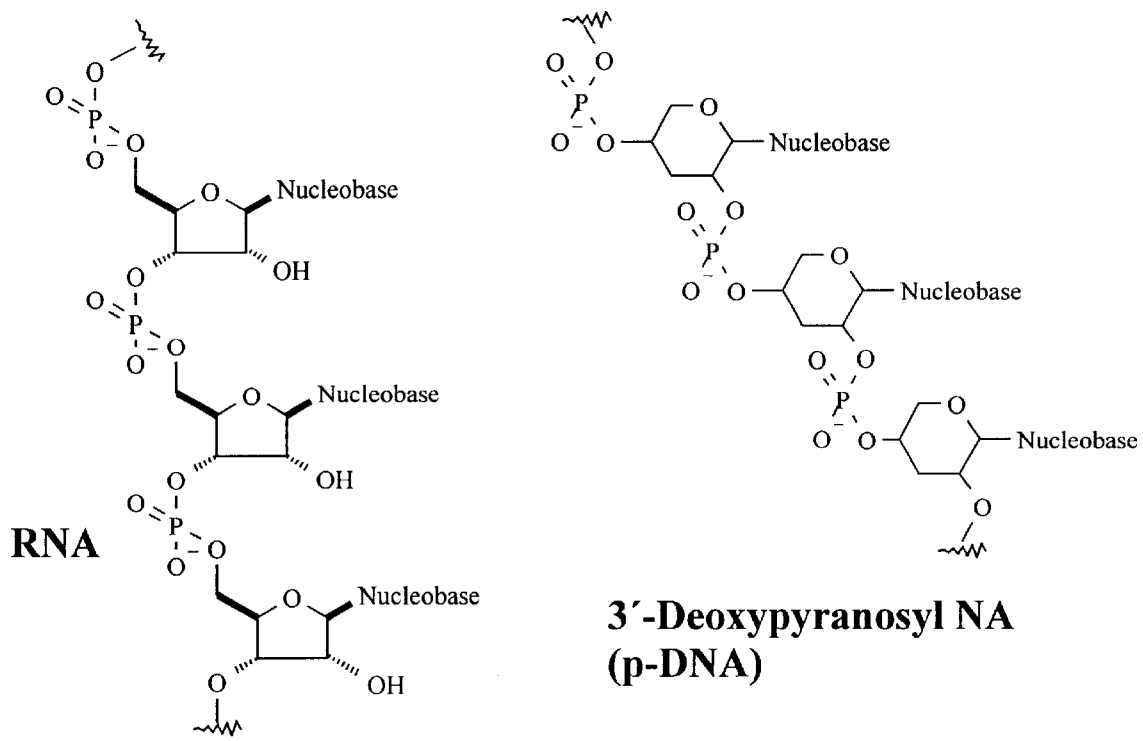
FIG. 3 shows a section from the structure of RNA in its naturally occurring form (left) and a p-DNA (right).
Figure 4:
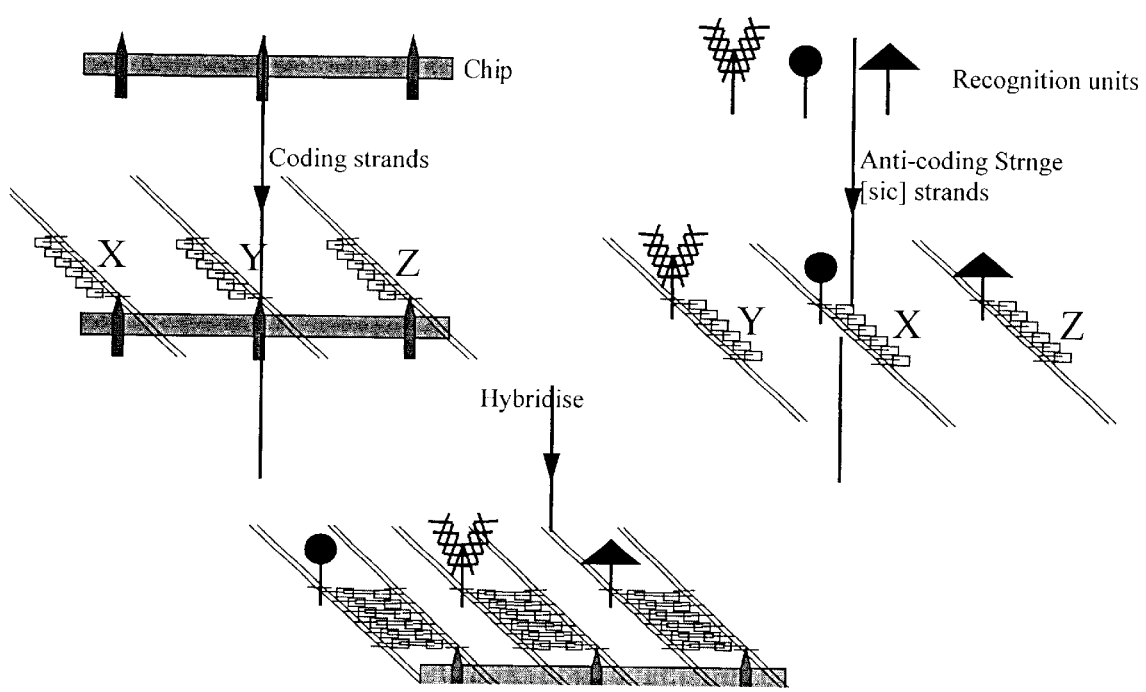
FIG. 4 schematically shows an arrangement of immobilized recognition structures (arrays) on a solid carrier.

1,2-O-Isopropylidene-3-O-[(methylthio) thiocarbonyl]-5-O-trityl-α-D-xylofuranose (3)

444.3 g (1.027 mol) of 1,2-O-isopropylidene-5-O-trityl-α-D-xylofuranose (2) were dissolved in 1000 ml of abs. DMF. 29.58 g (1.232 mol) of NaH were added in portions at 0–5° C. in the course of 1 h with cooling, KPG stirring, under an $N_2$ atmosphere and a gentle stream of $N_2$. After NaH addition was complete, the mixture was stirred for a further 15 minutes with cooling. It was additionally stirred for a further hour without cooling until hydrogen was no longer formed. The internal temperature of the clear solution was 12° C. 57.7 ml (1.027 mol) of carbon disulphide were then added dropwise in the course of 20 minutes. The reaction temperature was kept at 20–25° C. by cooling. After 30 minutes, 77.4 ml (1.027 mol) of iodomethane were added in the course of 20 minutes with gentle cooling (T=20–25° C.). During the reaction, a further 500 ml of DMF had to be added. After a further 2 h, the mixture was added to 2 l of ice water and 1.5 l of dichloromethane and extracted with stirring. The org. phase was extracted with 4×0.7 l of water, dried over $Na_2SO_4$, filtered and concentrated. 610.5 g of crude product were obtained, which was directly reacted further.

TLC (silica gel, acetone/heptane 1:4): $R_f$=0.30.

$^1$H NMR (300 MHz, $CDCl_3$): 1.32, 1.56 (2s, 3H, 2×$CH_3$), 2.41 (s, 3H, S—$CH_3$), 3.32 (dd, 1H, H—C(5)), 3.47 (dd, 1H, H—C(5)), 4.54 (m, 1H, H—C(4)), 4.64 (m, 1H, H—C(2)), 5.89 (m, 1H, H—C(3)), 6.09 (d, J=3 Hz, 1H, H—C(1)), 7.18–7.43 (m, 15H, $H_{arom}$).

Example 2

3-Deoxy-1,2,4-tri-O-benzoyl-α-D-erythropentose (6)

4.16 g (1 mmol) of 3-deoxy-1,2-O-isopropylidene-5-O-trityl-α-D-xylofuranose (4) were dissolved in 20.0 ml of dichloromethane. 20.0 ml of water and 2.0 ml of trifluoroacetic acid were added with stirring at RT and the mixture was stirred at RT for 17 h. The phases were separated, and the aqueous phase was extracted 2× using 20 ml of dichloromethane each time and concentrated somewhat. The residue was dissolved a further 2× in 20 ml of water in each case and concentrated. The residue was again dissolved in 20 ml of water, stirred with 2.0 g of strongly basic ion exchanger for 15 minutes (pH 7–8), the ion exchanger was filtered off and the filtrate was concentrated to dryness. The slightly yellowish oil was treated with 27 ml of abs. pyridine/dichloromethane 2:1, 2.0 g of molecular sieve 4 Å were added and the mixture was stirred under argon for 1 h. 6.1 ml of benzoyl chloride in 6.1 ml of abs. pyridine were then added dropwise at −30° C. After 1 hour, the mixture was allowed to come to room temperature and was stirred overnight. After the addition of 2 ml of MeOH, it was concentrated, and the solid residue was coevaporated with toluene, again taken up in toluene, stirred and filtered off. The filtrate was concentrated and purified on a silica gel column (silica gel 60, 4×33 cm) using a linear gradient of heptane to heptane/EtOAC 2:1 in 4 l. The product fractions obtained were concentrated, stirred in 30 ml of diethyl ether and the solid was filtered off with suction. 1.07 g (25%) of a white solid were obtained.

TLC (silica gel, dichloromethane/MeOH 4:1): $R_f$=0.45.

TLC (silica gel, heptane/EtOAc 2:1): $R_f$=0.35.

$^1$H NMR (300 MHz, $CDCl_3$): 2.51 (m, 2H, H—C(3)), 4.01 (dd, 1H, H—C(5)), 4.21 (dd, 1H, H—C(5)), 5.17 (m, 2H, H—C(4), H—C(2)), 6.38 (d, J=2 Hz, 1H, H—C(1)), 7.18–7.95 (m, 16 H, $H_{arom}$), 7.40 (m, 4H, $H_{arom}$), 7.52 (m, 1H, $H_{arom}$), 7.95 (m, 6H, $H_{arom}$).

$^{13}$C [lacuna] (300 MHz, $CDCl_3$): 27.28 (s, C(3)), 63.45 (s, C(5)), 65.56 (s, C(4)), 66.24 (s, C(2)), 91.202 (s, C(1)), 128.2–129.9 (m, 12$C_{arom}$), 133.07 (s, $C_{arom, para}$), 133.22 (s, $C_{arom, para}$), 133.71 (s, $C_{arom, para}$), 164.22 (s, C=O), 165.60 (s, C=O), 166.06 (s, C=O).

Example 3

Synthesis of 1-{3'-deoxy-4'-O-[(4,4 '-dimethoxytriphenyl)methyl]-β-D-ribopyranosyl}-thymine-2'-O-(2-cyanoethyl-N,N-disopropyl) phosphoramidite (10a)

Synthesis of 1-(3'-deoxy-2,4-di-O-benzoyl-β-D-ribopyranosyl)thymine (7a)

1.0 g (2.24 mmol) of 3'-deoxy-1,2,4-tri-O-benzoylribopyranose (6) and 283 mg (2.24 mmol) of thymine were suspended in 11.0 ml of acetonitrile and warmed to 60° C. 957 mg (4.7 mmol) of N,O-bis(trimethylsilyl) acetamide (BSA) were added dropwise to this mixture in the course of 10 minutes using a syringe and it was left at 60° C. for 15 min. 2.02 g (9.07 mmol) of trimethylsilyl trifluoromethanesulphonate (=TMS triflate) are added to the resulting solution in the course of 45 min and it is subsequently stirred at 60° C. for 2 h. The reaction mixture is allowed to cool to RT, and is diluted with EtOAc and extracted against dilute NaHCO$_3$ solution. The EtOAc phase was again extracted with water, dried over sodium sulphate, filtered and concentrated. By chromatography on silica gel 60 (3×28 cm) using a linear gradient of heptane to heptane/EA=1/1 in 4 l, after concentrating the product-containing fractions a colourless amorphous solid was obtained, which was taken up 20 ml of diethyl ether and stirred. 1.0 g (99%) of the desired product resulted.

TLC (silica gel, EtOAc/heptane 1:1): R$_f$=0.27.

$^1$H NMR (300 MHz, CDCl$_3$): 1.94 (d, 3H, CH$_3$), 2.12 (dd, 1H, H$_{eq}$—C(3')), 2.93 (m, 1H, H$_{ax}$—C(3')), 3.70 (t, 1H, H$_{eq}$—C(5')), 4.40 (m, 1H, H$_{ax}$—C(5')), 5.25 (m, 1H, H—C(4')), 5.32 (m, 1H, H—C(2')), 5.93 (d, J=9.3 Hz, 1H, H—C(1')), 7.22 (d, 1H, H—C(6)) 7.38–7.50 (m, 4H, 3,5-H$_{arom}$), 7.54–7.63 (m, 2H, 4-H$_{arom}$) 7.94–8.04 (m, 4H, 2,6-H$_{arom}$), 8.26 (bs, 1H, H—N(3)). $^{13}$C [lacuna] (300 MHz, CDCl$_3$): 12.52 (CH$_3$), 165.10 (C=O), 34.63 (C(3')), 65.85 (C(4')), 67.64 (C(2')), 69.16 (C(5')), 82.22 (C(1')), 111.94 (C(5)), 128.50 (C$_{arom}$), 128.54 (C$_{arom}$), 128.72 (C$_{arom}$), 129.21 (C$_{arom}$), 129.71 (C$_{arom}$), 129.85 (C$_{arom}$), 133.51 (C$_{arom}$), 133.63 (C$_{arom}$), 134.66 (C(6)), 150.69 (C(2)), 163.31 (C(4)), 165.34 (C=O).

Synthesis of 1-(3'-deoxyribopyranosyl)thymine (8a)

807 mg (1.79 mmol) of 1 were stirred at RT for 48 h in 20 ml of methanolic ammonia. The reaction solution was then concentrated, and the solid residue was stirred in EtOAc/MeOH=9:1 and filtered off with suction. 345 mg (80%) of a white crystalline solid were obtained. The mother liquor was concentrated and purified on a silica gel column (silica gel 60, 3×15 cm) using a linear gradient of EtOAc to EtOAc/MeOH=9:1 in 3 l. A further 70 mg (16%) of the desired product were obtained. Altogether, 415 mg (96%) of 2 were isolated.

TLC: (silica gel, EtOAc/MeOH 9:1) R$_f$=0.28

$^1$H-NMR (300 MHz, MeOD): 1.48 (q, 1H, H$_b$(3'), 1.80 (d, 3H, CH$_3$), 2.37 (m, 1H, H$_b$(3')), 3.20 (t, 1H, H$_b$(5')), 3.24 (m, 2H, OH), 3.70 (m, 1H, H(4')), 3.75 (m, 1H, H(2')), 3.90 (ddd, 1H, H$_a$(5')), 5.22 (d, 1H, J=9 Hz, H(1')), 7.37 (d, 1H, H(6)).

Synthesis of 1-{3'-deoxy-4'-O-[(4,4'-dimethoxytriphenyl)methyl]-β-D-ribopyranosyl}-thymine (9a)

320 mg (1.32 mmol) of 8a were dissolved in 6 ml of abs. dichloromethane/pyridine 1:2 under an N$_2$ atmosphere, 1 g of molecular sieve 4 Å was added and the mixture was stirred at RT for 15 min. It was cooled to −10° C., 0.47 ml of diisopropylamine and 0.76 g (2.24 mmol) of dimethoxytrityl chloride (DMTCl) were added [lacuna] come to RT. The mixture was stirred overnight. Repeated addition of 0.38 g (1.12 mmol) of DMTCl in 2 ml of abs. dichloromethane and stirring overnight completed the reaction. The mixture was filtered off from the molecular sieve, poured onto half-saturated NaHCO$_3$ solution and extracted with methylene chloride. The methylene chloride phase was extracted 2× by shaking with water, dried over Na$_2$SO$_4$, filtered and concentrated. It was purified on a silica gel column (silica gel 60; 3×20 cm) and a gradient (2 l of n-heptane and 2 l of n-heptane/EA=1/1 as a linear gradient). Finally, the column was washed with heptane/EtOAc/MeOH 5:5:1, and the product-containing fractions were concentrated in a rotary evaporator, stirred in 50 ml of carbon tetrachloride and concentrated again. The residue was dried overnight in a high vacuum. 352 mg (32%) of the doubly tritylated product 12a were obtained. The polar fractions were separated once more on a silica gel column (silica gel 60, 3×25 cm) using a linear gradient of dichlorometane to dichloromethane/MeOH 19=1 in 4 l. 50 mg (7%) of 1-{3'-deoxy-2'-O-[(4,4'-dimethoxytriphenyl)methyl]-β-D-ribopyranosyl}thymine 11a and 293 mg (41 %) of 9a were isolated.

TLC (silica gel): 9a (CH$_2$Cl$_2$/MeOH 19:1) R$_f$=0.26 11a (CH$_2$Cl$_2$/MeOH 19:1) R$_f$=0.29 12a (EtOAc/heptane 4:1) R$_f$=0.49

$^1$H-NMR (300 MHz, CDCl$_3$): 1.75 (s, 3H, CH$_3$), 2.20 (m, 1H, H$_{ax}$(3')), 2.92 (m, 1H, H$_{eq}$(3')), 3.11 (m, 2H, H(4'), H$_{ax}$—C(5')), 3.34 (m, 1H, H$_{eq}$(5')), 3.64 (m, 1H, H(2')), 3.71 (d, 6H, 2×OCH$_3$), 5.26 (d, 1H, J=9 Hz, H(1')), 6.76 (m, 4H, H$_{arom}$), 6.89 (d, 1H, H(6)), 7.10–7.44 (m, 9H, H$_{arom}$), 9.14 (bs, 1H, H—N(3))

Synthesis of 1-{3'-deoxy-4'-O-[(4,4'-dimethoxytriphenyl) methyl]-β-D-ribopyranosyl}-thymine-2'-O-(2-cyanoethyl-N,N-disopropyl)phosphoramidite (10a)

218 mg (0.4 mmol) of 1-{3'-deoxy-4'-O-[(4,4'-dimethoxytriphenyl)methyl]-β-D-ribopyranosyl}thymine 9a were dissolved in 2.0 ml of abs. dichloromethane and treated with 155 mg (1.2 mmol) of N-ethyldiisopropylamine. 237 mg (1.0 mmol) of mono(2-cyanoethyl) N,N-diisopropylchlorophosphoramidite were then added dropwise at RT in the course of two minutes. The mixture stirred 3 h at RT., was diluted with CH$_2$Cl$_2$ to 40 ml and extracted with 50 ml of phosphate buffer (pH=7), and the org. phase was dried over Na$_2$SO$_4$, filtered and concentrated. The crude product was purified on a silica gel column (3×15 cm) using a linear gradient of EA/heptane=1:2 to EA in 4 l. 266 mg (89%) of a colourless resin were obtained.

TLC (silica gel, heptane/EtOAc 4:1): R$_f$=0.47/0.54

$^1$H-NMR (400 MHz in CDCl$_3$): 1.10 (m, 6H, 2×CH$_3$); 1.83 (m, 1H, H$_{ax}$—C(3')); 1.88 (m, 3H, CH$_3$—C(5)); 2.21 (m, 1H, H$_{eq}$—C(3')); 2.41–2.61 (m, 2H, CH$_2$CN); 2.98 (m, 1H, H$_{eq}$—C(5')); 3.19 (m, 1H, H$_{ax}$—C(5')); 3.55–3.80 (m; 6H, CH$_2$OP, H—C(4'), H—C(2'); 2×CH); 3.8 (m, 6H, 2×CH$_3$); 5.41 (d, J=8.86 Hz, 1H, H—C(1')); 6.8 (m, 4H, H$_{DMT}$); 6.97 (m, 1H, H—C(6)); 7.20–7.52 (m, 9H, H$_{arom}$); 8.25 (s, 1H, H—N(3)).

Example 4

Synthesis of N$^6$-benzoyl-3-{3'-deoxy-4'-O-[(4,4'-dimethoxytriphenyl)methyl]-β-D-ribopyranosyl}adenine-2'-O-(2-cyanoethyl-N,N-disopropyl)phosphoramidite (10b)

Synthesis of N$^6$-benzoyl-3-(3'-deoxy-2,4-di-O-benzoylribopyranosyl)adenine (7b)

2.23 g (5 mmol) of 6 and 1.20 g (5 mmol) of N$^6$-benzoyladenine were treated in 35 ml of abs. acetonitrile under an argon atmosphere and the mixture was stirred for 15 minutes. It was heated to gentle reflux. 2.14 g (10.5 mmol) of BSA were added dropwise to this suspension in the course of 20 minutes and the mixture was stirred at 68° C. for 15 min. 4.7 g (18 mmol) of tin tetrachloride were then added dropwise in the course of 5 minutes and the mixture was stirred under reflux for 1 h. It was allowed to come to RT, poured onto 150 ml of saturated NaHCO$_3$ soln and extracted against 100 ml of EtOAc. The precipitate deposited was filtered off with suction and washed with 150 ml of EtOAc. The org. phase was again extracted by shaking with 100 ml of water, dried over sodium sulphate, filtered and concentrated. It was purified on a silica gel column (3×26 cm) using a gradient (2 l of EtOAc/heptane 2:1 and 2 l of EtOAc [lacuna] linear gradient), the product-containing batches were combined and 2.7 g (96%) of a white solid were isolated.

TLC (silica gel): 4 (EtOAc): $R_f$=0.40.

$^1$H-NMR (300 MHz, CDCl$_3$): 2.16 (m, 1H, H(3')), 2.97 (m, 1H, H$_{eq}$(3')), 3.76 (m, 1H, H$_{ax}$(5')), 4.41 (m, 1H, H$_{eq}$(5')), 5.38 (m, 1H, H(4')), 5.62 (m, 1H, H(2')), 5.98 (d, 1H, J=8.92 Hz, H(1')), 7.22–8.0 (m, 15H, H$_{arom}$), 8.21 (s, 1H, H(8)), 8.74 (s, 1H, H(2)), 8.91 (bs, 1H, NH). $^{13}$C-NMR (300 MHz, CDCl$_3$): 34.57 (C(3')), 65.80 (C(4')), 68.86 (C(2')), 69.13 (C(5')), 82.67 (C(1')), 122.53 (C(6)), 127.76–133.62 (12×C(arom)), 140.62 (C(8)), 149.63 (C(6)), 151.91 (C(4)), 153.03 (C(2)), 164.44 (C=O on N—C(6)), 164.77 (C=O), 165.32 (C=O).

Synthesis of N$^6$-benzoyl-3-(3'-deoxy-β-D-ribopyranosyl) adenine (8b)

280 mg (0.5 mmol) of 7b were dissolved in 7 ml of THF/MeOH/H$_2$O 5:4:1 and, cooled to –5° C. and 2.22 ml of 32% strength NaOH solution in THF/MeOH/H2O 5:4:1 were slowly added such that the temp. remained below 0° C. The mixture was stirred for 20 min with cooling, treated with 400 mg (7.5 mmol) of ammonium chloride and the solution was allowed to come to RT. The solvents were stripped off, the residue was dissolved in 20 ml of MeOH, and the solution was absorbed in 10 g of silica gel and purified by chromatography on a silica gel column (3×12 cm with 1 l of dichloromethane and 2 l of CH$_2$Cl$_2$/MeOH=4/l as a linear gradient). 157 mg (88%) of the colourless solid 8b were isolated.

TLC (silica gel): 5 (EtOAc/MeOH 4:1) $R_f$=0.34

$^1$H-NMR (300 MHz, MeOD): 1.58 (q, 1H, H$_{ax}$(3')), 2.45 (m, 1H, H$_{eq}$(3')), 3.33 (m, 1H, H$_{ax}$(5')), 3.87 (m, 1H, H(4')), 3.97 (m, 1H, H$_{eq}$(5')), 4.25 (m, 1H, H(2')), 5.40 (d, 1H, J=9.2 Hz, H(1')), 7.30–8.02 (m, 5H, H$_{arom}$), 8.47 (s, 1H, H(8)), 8.63 (s, 1H, H(2)).

Synthesis of N$^6$-benzoyl-3-{3'-deoxy-4'-O-[(4,4'-dimethoxytriphenyl)methyl]-β-D-ribopyranosyl }adenine (9b)

1.02 g (2.87 mmol) of 8b were dissolved in 9.0 ml of abs. pyridine in an argon atmosphere, 1.56 g (12 mmol) of N-ethyldiisopropylamine and 1.0 g of molecular sieve 4 Å were added and the mixture was stirred at RT for 30 min. It was then cooled to –10° C. and 2.2 g (6.49 mmol) of DMTCl dissolved in 5.0 ml of abs. chloroform were added dropwise in the course of 30 min. The experiment stirred at RT overnight. After 22 h, 200 mg (0.59 mmol) of DMTCl and, 2 h afterwards, a further 430 mg (1.27 mmol) of DMTCl were again added in solid form. After a further 22 h at RT, the mixture was poured onto 100 ml of a half-saturated NaHCO$_3$ soln, treated with 100 ml of methylene chloride and extracted. The org. phase was additionally reextracted 2× with 100 ml of H$_2$O each time, dried over Na$_2$SO$_4$, filtered and concentrated. Purification on a silica gel column (3×25 cm) using a gradient (2 l of EtOAc/heptane 2:1 and 2 l EtOAc with a linear gradient) yielded: 520 mg (27.5%) of 9b, 430 mg (23%) of mixture of 9b and 11b, 370 mg (13.4%) of 12b and 370 mg (20%) of the starting material.

TLC (silica gel, EtOAc): 9b: $R_f$=0.29 11b: $R_f$=0.12 12b: $R_f$=0.55

$^1$H-NMR (500 MHz in CDCl$_3$): 1.92 (m, 1H, H$_{ax}$(3')), 2.42 (m, 1H, H$_{eq}$(3')), 2.99 (m, 1H, H$_{eq}$(5')), 3.21 (m, 1H, H$_{ax}$(5')), 3.79 (d, 6H, 2×OCH$_3$), 3.84 (m, 1H, H(4')), 4.13 (m, 1H, H(2')), 5.17 (bs, 1H, OH), 5.32 (d, 1H, J=8.7 Hz, H(1')), 6.86 (dd, 4H, H$_{arom}$), 7.20–7.75 (m, 12H, H$_{arom}$), 7.96 (m, 3H, 1H, (8), 2H$_{arom}$), 8.54 (s, 1H, H(2)), 8.94 (bs, 1H, NH). $^{13}$C-NMR (500 MHz in CDCl$_3$) 39.13 (C(3')), 55.26 (2×OCH$_3$), 66.59 (C(4')), 67.72 (C(2')), 70.76 (C(5')), 86.69 (C$_{tert\ trityl}$), 86.93 (C(1')), 113.31 (2C$_{arom}$), 113.34 (2C$_{arom}$), 121.8 (C(5)), 127.04–136.74 (11C$_{arom}$), 141.74 (C(8)), 145.51 (C$_{arom}$), 148.85 (C(6)), 151.56 (C(2)), 158.74 (2C$_{arom}$), 164.61 (C=O).

Synthesis of N$^6$-benzoyl-3-{3'-deoxy-4'-O-[(4,4'-dimethoxytriphenyl)methyl]-β-D-ribopyranosyl}adenine-2'-O-(2-cyanoethyl-N,N-disopropyl)phosphoramidite (10b)

380 mg (0.58 mmol) of N$^6$-benzoyl-3-{3'-deoxy-4'-[(4,4'-dimethoxytriphenyl)methyl]-β-D-ribopyranosyl}adenine 9b were dissolved in 2.0 ml of abs dichloromethane and treated with 224 mg (1.73 mmol) of N-ethyldiisopropylamine. 342 mg (1.44 mmol) of mono-(2-cyanoethyl) N,N-diisopropylchlorophosphoramidite were then added dropwise in the course of two minutes. The mixture stirred 3 h at RT, was diluted to 40 ml with CH$_2$Cl$_2$ and extracted with 50 ml of phosphate buffer (pH=7). The org. phase was dried over Na$_2$SO$_4$, filtered and concentrated. The residue was purified [lacuna] silica gel column (3×15 cm) using a linear gradient of EtOAC/heptane (1:2) to EtOAc/heptane (4:1) as a linear gradient. 400 mg (80%) of a yellowish foam were obtained.

TLC (silica gel, EtOAc/heptane 4:1): $R_f$=0.38

$^1$H-NMR (400 MHz in CDCl3): 1.05 (m, 6H, 2×CH$_3$); 1.87 (m, 1H, H$_{ax}$—C(3')); 2.23 (m, 1H, H$_{eq}$—C(3')); 2.32 & 2.55 (2×2H, CH$_2$CN); 3.05–3.70 (m, 6H, 2×CH, CH$_2$OP, 2×H—C(5')); 3.79 (m, 6H, 2×OCH$_3$); 3.90 (m, 1H, H—C(4')); 4.12 (m, 1H, H—C(2')); 5.47 (2×d, J=8.87Hz, 1H, H—C(1')); 6.85 (m, 4H, H$_{DMT}$); 7.20–7.65 (m, 13H, H$_{arom}$); 8.0 (m, 2H, H$_{arom}$); 8.09 (s, 1H, H—C(8)); 8.80 (s, 1H, H—C(2)); 8.97 (s, br, 1H, HN).

Synthesis of N$^6$-benzoyl-3-{3'-deoxy-4'-O-[(4,4'-dimethoxytriphenyl)methyl]-β-D-ribopyranosyl}adenine-2'-O-succinoyl (13b)

115 mg (0.174 mmol; 1 eq) of N$^6$-benzoyl-3-{3'-deoxy-4'-O-[(4,4'-dimethoxytriphenyl)-methyl]-β-D-ribopyranosyl}adenine (9b) were stirred at RT for 2½ h together with 35 mg (0.35 mmol; 2 eq) of succinic anhydride and 25 mg (0.21 mmol; 1.2 eq) of DMAP in 1.0 ml of abs CH$_2$Cl$_2$ under an N$_2$ atmosphere. The mixture was then diluted to 20 ml with methylene chloride, and extracted 1× with 20 ml of 10% strength citric acid and 3× with 20 ml of water each time. The org. phase was dried over sodium sulphate, filtered and concentrated. 130 mg (99%) of 13b were obtained.

TLC (silica gel, EtOAc/MeOH 19:1): $R_f$=0.14

$^1$H-NMR (500 MHz, CDCl$_3$): 1.82 (m, 1H, H$_{ax}$(3')), 2.20 (m, 2H, 2×CH$_2$), 2.32 (m, 1H, H$_{eq}$(3')), 3.02 (m, 1H, H$_{eq}$(5')), 3.30 (m, 1H, H$_{ax}$(5')), 3.73 (d, 6H, 2×OMe), 3.82 (m, 1H, H(4')), 5.06 (m, 1H, H(2')), 5.55 (d, J=9.5 Hz, 1H, H(1')), 6.79 (m, 4H, o to OMe), 7.14–7.49 (m, 12H, 9H$_{trityl}$, 3H$_{Bz}$), 7.87–7.91 (m, 2H, 2H$_{Bz}$), 7.94 (s, 1H, H—C(8)), 8.55 (s, 1H, H(2)), 9.6 (bs, 1H, —COOH).

What is claimed is:

1. A 3'-deoxypentopyranosylnucleoside having a structure of the formula:

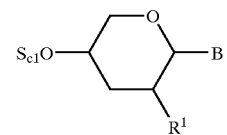

wherein R$^1$ is selected from the group consisting of H, OH, Br, Cl,

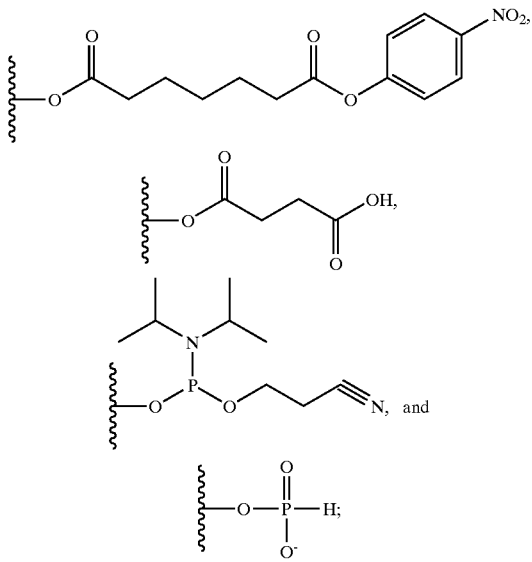

wherein ⟨ is the point of attachment;
wherein $S_{c1}$ is selected from the group consisting of H, acyl group, trityl group, allyloxycarbonyl group, photolabile protective group, and β-eliminable protective group; and
wherein B is selected from the group consisting of 9-adeninyl, 9-guaninyl, 1-thyminyl, 1-cytosinyl, 1-uracilyl, and 1-indolyl, with the proviso that, where B is 1-cytosinyl, $R^1$ is not Br, is not OH, and is not H; and where B is 9-adeninyl, $R^1$ is not OH.

2. The nucleoside according to claim 1, wherein the sugar of the 3'-deoxypentopyranosylnucleoside is in the D configuration.

3. The nucleoside according to claim 1, wherein the sugar of the 3'-deoxypentopyranosylnucleoside is in the L configuration.

4. The nucleoside according to claim 1, wherein the 3'-deoxypentopyranosylnucleoside is selected from the group consisting of ((2',4'-di-O-benzoyl)-3'-deoxy-β-ribopyranosyl)nucleoside; N-benzoyl-2',4'-di-O-benzoyl-3'-deoxyribopyranosylnucleoside; N-isobutyryl-2',4'-di-O-benzoyl-3'-deoxyribopyranosylnucleoside; $O^6$-(2-(4-nitrophenyl)ethyl)-$N^2$-isobutyryl-2',4'-di-O-benzoyl-3'-deoxyribopyranosyl guanine; 3'-deoxy-β-ribopyranosylnucleoside, $N^2$-isobutyryl-3'deoxy-β-ribopyranosyl guanine; $O^6$-(2-cyanoethyl)-$N^2$-isobutyryl-3'deoxy-β-ribopyranosyl guanine; $O^6$-(2-(4-nitrophenyl)ethyl)-$N^2$-isobutyryl-3'deoxy-β-ribopyranosyl guanine; 4'-DMT-3'-deoxypentopyranosylnucleoside; 4'-DMT-3'-deoxyribopyranosylnucleoside; N-benozyl-4'-DMT-3'-deoxyribopyranosylnucleoside; N-isobutyroyl 4'-DMT-3'-deoxyribopyranosylnucleoside; $O^6$-(2-cyanoethyl)-$N^2$-isobutyryl-4'-DMT-3'-deoxyribopyranosyl guanine; $O^6$-(2-(4-nitrophenyl)ethyl-$N^2$-isobutyryl-4'-DMT-3'-deoxyribopyranosyl guanine; 3'-deoxy-β-ribopyranosyl-N,N'-dibenzoyladenine; and 3'-deoxy-β-ribopyranosyl-N,N'-dibenzoylguanine;

wherein the nucleobase is selected from the group consisting of adenine, thymine, guanine, and cystosine;
wherein the nucleobase is bonded to the pyranose at the anomeric carbon; and
with the proviso that, when the nucleobase is adenine, the point of attachment to the base is N9, when the nucleo-base is thymine, the point of attachment to the base is N1, when the nucleobase is guanine, the point of attachment to the base is N9, and when the nucleobase is cytosine, the point of attachment to the base is N1.

5. The nucleoside according to claim 1, modified by the addition of a linker bonded to substituent B.

6. The nucleoside according to claim 5, wherein the nucleoside and linker have the formula:

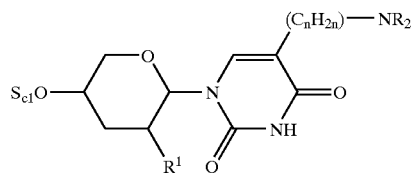

wherein n is an integer from 1–12, and wherein R is an H or a linear or branched, optionally substituted alkyl, aryl, or acyl group.

7. The nucleoside according to claim 6, wherein $R_2$ is a phthaloyl group.

8. The nucleoside according to claim 5, wherein B has the formula:

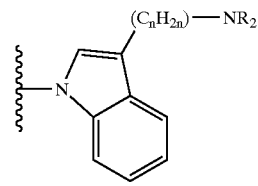

wherein n is an integer from 1–12, and wherein R is an H or a linear or branched, optionally substituted alkyl, aryl, or acyl group; and
wherein ⟨ is the point of attachment.

9. The nucleoside according to claim 8, wherein $R_2$ is a phthaloyl group.

10. An oligomer of the structure A:

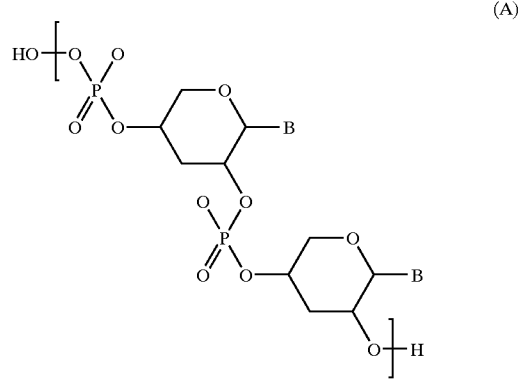

(A)

wherein B is selected from the group consisting of 9-adeninyl, 9-guaninyl, 1-thyminyl, 1-cytosinyl, 1-uracilyl, and 1-indolyl.

11. A process for the preparation of a 3'-deoxypentopyranosyl oligomer, comprising the steps of:
(a) bonding a 4'-protected-3'-deoxypentopyranosyl nucleoside to a solid support by coupling of the 2'-OH with a CPG support or other similar support with an amide linkage;

(b) deprotecting the 4'-protected-3'-deoxypentopyranosyl nucleoside bonded to the solid support in step (a), wherein the deprotection takes place in the 4'-position;

(c) reacting the 2'-OH group of the reaction product from step (b) with a 4'-protected-3'-deoxypentopyranosyl nucleoside phosphoramidite in the presence of a coupling reagent;

(d) oxidizing the reaction product of step (c); and (e) repeating steps (b) and (d) one or more times to produce the desired length of oligomer.

12. The process according to claim 11, further comprising removing the protective groups from the product of step (d).

13. The process according to claim 11, wherein the coupling reagent is pyridinium hydrochloride.

14. The process according to claim 11, further comprising the steps of:

(f) deprotecting the 4'-protected-3'-deoxypentopyranosyl nucleotide at the 4'-OH position;

(g) reacting the product of step (e) with a protected furanosyl nucleoside phosphoramidite;

(h) deprotecting the protected furanosyl nucleotide;

(i) repeating steps (g) and (h) one or more times to produce the desired length of oligomer.

15. The process according to claim 14, further comprising removing the protective groups from the product of step (h).

* * * * *

UNITED STATES PATENT AND TRADEMARK OFFICE
CERTIFICATE OF CORRECTION

| | | |
|---|---|---|
| PATENT NO. | : 6,696,555 B1 | Page 1 of 1 |
| APPLICATION NO. | : 09/762977 | |
| DATED | : February 24, 2004 | |
| INVENTOR(S) | : Christian Miculka, Thomas Wagner and Norbert Windhab | |

It is certified that error appears in the above-identified patent and that said Letters Patent is hereby corrected as shown below:

IN THE TITLE PAGES and Col. 1 line 1:
In Item (54), please replace "3'-Desoxypentopyranosyl" with --3'-Deoxypentopyranosyl--

IN THE CLAIMS:
Please replace claim 11 with the following claim:

Col. 18, line 62 through col. 19, line 10
11. A process for the preparation of a 3'-deoxypentopyranosyl oligomer, comprising the steps of:
(a) bonding a 4'-protected-3'-deoxypentopyranosyl nucleoside to a solid support by coupling of the 2'-OH with a CPG support or other similar support with an amide linkage;
(b) deprotecting the 4'-protected-3'-deoxypentopyranosyl nucleoside bonded to the solid support in step (a), wherein the deprotection takes place in the 4'-position;
(c) reacting the 4'-OH group of the reaction product from step (b) with a 4'-protected-3'-deoxypentopyranosyl nucleoside phosphoramidite in the presence of a coupling reagent;
(d) oxidizing the reaction product of step (c); and
(e) repeating steps (b) through (d) one or more times to produce the desired length of oligomer.

Signed and Sealed this

Twenty-sixth Day of May, 2009

JOHN DOLL
*Acting Director of the United States Patent and Trademark Office*